United States Patent [19]
Muller

[11] Patent Number: 5,613,965
[45] Date of Patent: Mar. 25, 1997

[54] CORNEAL REPROFILING USING AN ANNULAR BEAM OF ABLATIVE RADIATION

[75] Inventor: David F. Muller, Boston, Mass.

[73] Assignee: Summit Technology Inc., Waltham, Mass.

[21] Appl. No.: 351,826

[22] Filed: Dec. 8, 1994

[51] Int. Cl.$^6$ ........................................................ A61N 5/02
[52] U.S. Cl. .................................... 606/5; 606/2; 606/10; 606/14
[58] Field of Search ...................... 606/2, 3–18; 359/642, 359/654, 668

[56] References Cited

U.S. PATENT DOCUMENTS

| | | |
|---|---|---|
| 4,724,522 | 2/1988 | Belgorod . |
| 4,729,372 | 3/1988 | L'Esperance, Jr. ........................ 606/5 |
| 4,887,592 | 12/1989 | Loertscher ................................. 606/5 |
| 4,941,093 | 7/1990 | Marshall et al. . |
| 4,973,330 | 11/1990 | Azema et al. ............................. 606/5 |
| 4,994,058 | 2/1991 | Raven et al. .............................. 606/5 |
| 5,019,074 | 5/1991 | Muller . |
| 5,102,409 | 4/1992 | Balgorod . |
| 5,152,759 | 10/1992 | Parel et al. . |
| 5,256,853 | 10/1993 | McIntyre . |
| 5,281,211 | 1/1994 | Parel et al. . |

FOREIGN PATENT DOCUMENTS

| | | |
|---|---|---|
| 1210128 | 8/1986 | Canada . |
| 0467775 | 1/1992 | European Pat. Off. . |
| 0525902 | 7/1992 | European Pat. Off. . |
| WO91/04829 | 4/1991 | WIPO . |

OTHER PUBLICATIONS

Rioux, M. et al. (1978) "Linear, annular, and radial focusing with axicons and applications to laser machining" *Applied Optics* 17 (10): 1532–1536.

*Primary Examiner*—David M. Shay
*Attorney, Agent, or Firm*—Lahive & Cockfield; Thomas J. Engellenner; Peter J. Rainville

[57] ABSTRACT

Methods and systems are disclosed for corneal reprofiling employing an annular beam of ablative radiation to correct refractive errors in vision, and/or create "blend zones" in order to reduce any surface discontinuities on the cornea following hyperopia-correcting or astigmatism-correcting procedures. Preferably, the methods and systems of the present invention also operate to change the intensity distribution of the light beam, such that the annulus of radiation has a varying intensity as a function of radius and, thereby, achieves a blending or other desired effect with the least number of pulses. Methods of photorefractive keratectomy (PRK) are disclosed, including the steps of (a) selectively reprofiling a cornea of an eye by removing a volume of corneal tissue with ablative radiation to form a reprofiled region in the optical zone which steepens, at least in part, the central curvature of the cornea; and (b) applying to a peripheral region of the cornea an annular beam of ablative radiation having an intensity which varies radially from a inner to a outer segment of the annular beam to create a blend zone, thereby providing a smooth transition between the repro filed region and an unablated region of the cornea. Optical lens elements also are disclosed having a generally conic front face and a rear face which is generally perpendicular to the path of the incident beam. Light passing through this optical element will be refracted into an annular beam. Variations in the intensity profile of the annular beam can be introduced by employing an initial beam which has a non-uniform profile, or by modifying the shape of either the front face or the rear face of the optical element.

13 Claims, 5 Drawing Sheets

CORNEAL REPROFILING USING AN ANNULAR BEAM OF ABLATIVE RADIATION

BACKGROUND OF THE INVENTION

The technical field of this invention is corneal surgery and, in particular, the invention relates to systems and methods of repro filing the cornea of an eye by application of ablative radiation.

Recently, it has been demonstrated that changes in the refractive power of the eye can be achieved by laser ablation of the corneal surface. Such procedures, known as photorefractive keratectomy (PRK), involves the use of a nonthermal, high energy, laser radiation to sculpt the cornea into an ideal shape. For details, see, Marshall et al. "Photoablative Repro filing of the Cornea using an Excimer Laser: Photorefractive Keratectomy," Vol. 1, Lasers in Ophthalmology, pp. 21–48 (1986); and Tuff et al. "Stromal Remodeling Following Photorefractive Keratectomy," Vol. 1, Lasers in Ophthalmology, pp. 177–183 (1987), herein incorporated by reference.

The cornea of the eye comprises transparent avascular tissue. The cornea functions as both a protective, anterior membrane and a "window" through which light passes as it proceeds to the retina. The cornea is composed of a set of distinct layers: the outer epithelium, an anterior elastic lamina known as "Bowman's membrane," the cornea proper (or "stroma"), a posterior elastic lamina known as "Descemet's membrane", and the inner endothelium. The stroma is fibrous and constitutes the major portion of the cornea. Bowman's membrane, which forms the outer elastic lamina, is a rigid fibrillar structure not tending to cut or fracture, while Descemet's membrane, which forms the inner elastic lamina, is very brittle but elastic and has a tendency to curl. Together, the Bowman's and Descemet's membranes impart the necessary curvature to the stromal tissue. This curvature of the cornea constitutes an major component of the refractive power of the eye, thereby allowing objects to be imaged onto the retina.

The average adult cornea is about 0.65 mm thick at the periphery, and about 0.54 mm thick in the center. Photorefractive keratectomy involves sculpting the uppermost regions of the cornea, namely, the epithelium, Bowman's membrane, and the outer stroma. The epithelium consists of five or six layers of cells, and the underlying Bowman's membrane, is also a very thin structure. The corneal stroma accounts for about 90 percent of the corneal thickness. In performing PRK operations on the cornea, care must be taken to avoid damaging the underlying Descemet's membrane or endothelium.

In photorefractive keratectomies, a laser photoablation apparatus is used to change the curvature of the cornea, at least in the so-called "optical zone" or region of the cornea through which light must pass to enter the pupil and reach the retina. The size of the optical zone will, of course, vary from individual to individual, and will also vary based upon ambient light conditions (because the pupil will dilate and contract in response to ambient light). The extent of the sculpted region (and the depth of ablation) will depend on the amount of correction needed to achieve optimal vision. For example, correction of relatively mild myopia (nearsightedness) on the order of 2 Diopters requires only a modest flattening of the corneal curvature, which can be accomplished in a region of small cross-sectional area (e.g., affecting a circular region of the cornea in front of the pupil less than 5 millimeters in diameter). However, when more complicated refractive errors, such as more severe myopia, hyperopia (farsightedness) or astigmatisms, are corrected by PRK procedures, the sculpted area will extend across a much larger portion of the cornea, e.g., affecting a region as large as 8 mm in diameter or more.

One approach to performing PRK procedures is to employ an optical system which varies the size of the exposure area over time to effect a new profiling as the result of accumulated ablation steps. In one embodiment of such a "variable exposure area" system, a beam-shaping stop or window is moved axially along the beam to increase or decrease the region of cornea on which the laser radiation is incident. By progressively varying the size of the exposed region, a desired photoablation profile is established on the surface. For further details on this technique, see U.S. Pat. No. 4,941,093 issued to Marshall et al. on Jul. 10, 1990, herein incorporated by reference.

Another new technique for corneal reshaping involves the use of a beam-shaping mask which is disposed between the laser and the surface. In one embodiment, the mask provides a predefined profile of resistance to erosion by laser radiation whereby a portion of the laser radiation is selectively absorbed and another portion is transmitted to the surface in accordance with the mask profile. For further disclosures of such masking techniques, see U.S. Pat. No. 4,856,513 issued to Muller on Aug. 15, 1989; U.S. Pat. No. 4,994,058 issued to Raven et al. on Feb. 19, 1991; U.S. Pat. No. 5,019,074 issued to Muller on May 28, 1991, and U.S. Pat. No. 5,324,281, issued to Muller on Jun. 28, 1994, all of which are incorporated herein by reference.

To correct hyperopia, in particular, it is necessary to increase (steepen) the curvature of the cornea. This can be accomplished with either a movable stop system, using a stop which blocks the central portion of the beam, or with a beam-shaping mask which transmits an annulus of light. In the moving stop system, the inner diameter of the annulus typically is varied such that more light is transmitted to the periphery of the cornea. Similarly, with an erodible mask or the like, the mask operates to transmit an annulus of varying width over time with the same effect.

Hyperopia correction, which can require significant sculpting in a ring-like region having a diameter of about 4 mm to 8 mm, places additional demands on the engineering design of PRK apparatus, which normally must be met by increasing the size and/or power of the laser source. Increasing the power of the laser to compensate for inefficiencies in beam deliver is undesirable because large annular beams deliver a larger total amount of energy to the cornea per pulse.

Moreover, in performing hyperopia and/or astigmatic corrections, it is also often desirable to create a "blend zone" at the periphery of the sculpted region. Such blend zones provide an edge-smoothing effect where there would otherwise be a sharp circular (or elliptical) recess of a depth proportional to the magnitude of dioptric correction. Because sharp edges tend to induce regression of the reprofiled curvature, a blend zone provides an outer, profile-smoothing, region contiguous with the curvature-corrected zone. However, this blend zone further taxes the PRK apparatus because the zone must be created, at least in part, beyond the outer edge of the sculpted region and therefore can extend the overall diameter of the reprofiled region to as large as 10 millimeters. The need for a blend zone further fuels demand for laser beams having large and uniform cross-sectional fluences.

In addition, the formation of a blend zone at the outer periphery of the reprofiled cornea typically requires a reverse procedure, at least when a movable stop is employed, to perform hyperopia and/or astigmatic corrections. Either a different type of stop or an adjustable iris-type mechanism typically is used to deliver an annular pattern of radiation of progressively decreasing intensity to the outermost portions of the blend zone. This second stage in the procedure typically doubles the overall time that a patient must remain motionless with his or her eye aligned with the apparatus.

There exists a need for better PRK apparatus for refractive correction of myopia, hyperopia and/or astigmatism, as well as creation of blend zones, without resort to larger lasers. There also exists a need for systems that can achieve desired blend zones at the periphery of hyperopic or astigmatic correction regions with less waste of laser energy. In addition, a PRK system that could facilitate simplified and/or quicker formation of peripheral blend zones would satisfy a long-felt need in the art.

SUMMARY OF THE INVENTION

A system is disclosed for corneal reprofiling which generates and directs an annular pattern of ablative radiation onto a cornea. In particular, the annular beam can be used to provide hyperopia correction, and/or also can be used to create a "blend zone" in order to reduce any surface discontinuities on the cornea following hyperopia-correcting procedures.

The present invention permits ablation of the peripheral portions of the cornea in broad annular patterns without wasting a major component of the beam, and without resort to larger or more powerful lasers. The term "peripheral region" or "periphery" as used herein with reference to the cornea is intended to describe that portion of the cornea which forms the boundary between the reprofiled central region of the cornea and the surrounding unabated region. As such, it encompasses the unablated or minimally ablated regions adjacent to the central portion, or optical zone, where photorefractive keratectomy is performed.

Preferably, the system of the present invention also operates to change the intensity distribution of the light beam, such that the annulus of radiation has a varying intensity as a function of radius and, thereby, achieves a blending effect with the least number of pulses.

As used herein the terms "annular" and "annulus" are used to denote ring-like patterns of radiation of generally circular, elliptical or oval shape. The term "variable intensity" is intended to encompass beams of radiation that vary in energy or fluency across their cross-section. For example, in the case of an annular beam, the intensity can vary radially from a higher relative intensity (and, hence, ablative power) at an inner segment of the ring to a lower intensity at the outer or peripheral segment of the annulus.

Variations in ablative power of the annular beam of the present invention need not be linear or even unidirectional (e.g. progressively increasing or decreasing). In one embodiment, a non-linear variable intensity annulus of ablative radiation is disclosed which is particularly useful in creating the "blend zone" at the periphery of the optical zone of the cornea during a hyperopia correcting procedure. In this embodiment, the intensity of the ablative radiation is ideally low or close to zero at the inner segment of the annulus but rapidly increases to a peak value and then progressively tapers off at the outer edge of the ablative ring.

Other variations in intensity profile can be employed by those skilled in the art for particular applications. For example, the shape of the intensity profile can be further modified to complement the basic repro filing procedure, such that the two ablative operations achieve a cumulative effect that results in a smooth profile. Thus, the annular intensity profile itself might not achieve a smooth transition if applied alone to the cornea, but instead provides a second order effect which, when combined with the sculpting action of the corrective operations, achieves a desired blending effect in the boundary region between the reprofiled region and the unablated peripheral cornea.

In another aspect of the invention, a class of optical elements are disclosed which can be used to generate the annular beams of the present invention. In particular, lens elements are disclosed having a generally conic front face and a rear face which is generally perpendicular to the path of the incident beam. Light passing through this optical element will be refracted into an annular beam. Variations in the intensity profile of the annular beam can be introduced by employing an initial beam which has a non-uniform profile, or by modifying the shape of either the front face or the rear face of the optical element. For example, by using an appropriately design conical front face and introducing a slight convex curve to the rear face, an annular beam having a progressively decreasing intensity (from inner to outer ring segments) can be obtained.

In yet another aspect of the invention, PRK systems are disclosed which employ a first beam-shaping assembly to repro file the corneal curvature across at least a major portion of the central optical zone, and a second beam-shaping assembly which generates an annular pattern to generate edge-smoothing effects at the corneal periphery.

According to yet a further aspect of the invention, methods of photorefractive keratectomy are disclosed, including the steps of (a) selectively reprofiling a cornea of an eye by removing a volume of corneal tissue with ablative radiation from a central region of the cornea to form a repro filed region in the optical zone which steepens, at least in part, the central curvature of the cornea; and (b) applying to a peripheral region of the cornea an annular beam of ablative radiation having an intensity which varies radially from a inner to a outer segment of the annular beam to create a blend zone which provides a smooth transition between the repro filed region and an unablated region of the cornea. (It should be appreciated that the order of steps (a) and (b) is interchangeable.)

The invention will next be described in connection with certain illustrated embodiments; however, it should be clear that those skilled in the art can make various modifications, additions and subtractions without departing from the spirit or scope of the invention. For example, the formation of an annular ablation beam is described in connection with certain transmissive lens elements; however, it should be clear that equivalent beam-forming techniques can be obtained with reflective elements, or combinations of transmissive and reflective elements. Various other optical systems can be used as well, including, binary/diffractive optics, catadioptric optics, and Fresnel lens systems, to obtain an annular beam.

The invention also can be used for procedures other than simply corneal reprofiling. For example, the present invention can be practiced in connection with corneal transplants where a donor button is inserted into the patient's eye. As part of such a procedure, the transplanted cornea can be reprofiled and then a blend zone created to smooth any discontinuities resulting from either the reprofiling or the juncture of the donor button and the corneal transplant bed. In addition, the present invention can be used in the course of laser-assisted, automated lamellar keratoplasty where a portion of the cornea (e.g., the epithelium, Bowman's membrane and the outermost layers of the stroma) is removed, a reprofiling procedure is then performed in the exposed stroma, and the excised layer is then reattached to the reprofiled surface of the corneal stroma. In this approach, the annular exposure beam can be used effectively to ensure that the reprofiled stromal tissue does not have boundary effects that would prohibit reattachment of the excised cap structure.

BRIEF DESCRIPTION OF THE DRAWINGS

The invention will now be described by way of example with reference to the accompanying drawings, like reference characters on the drawings indicating like parts in several figures, in which.

DETAILED DESCRIPTION

The present invention can be practiced in conjunction with general photorefractive keratectomy (PRK) to provide an overall reprofiling of the corneal surface to correct hyperopia and/or astigmatism. In general, hyperopic conditions can be corrected by imparting a steeper curvature to the cornea overall. This can be achieved by exposing the optical zone generally (i.e., the central region of the cornea, approximately 2 millimeters to about 7 millimeters in diameter) to a succession of pulses of light energy while controlling the area exposed by each pulse, so as to successively change the exposure area.

If an increase in convexity is required (e.g., to correct hyperopia), the peripheral regions are exposed to a greater extent than the central region, thereby leaving a "bulge" in the middle of the cornea by selective application of laser energy. In the practice of the present invention, hyperopia would be corrected by reprofiling the cornea to provide normal visual acuity over most of the optical zone. However, at the edge of the reprofiled region, a rim-like discontinuity will be created in the corneal surface.

Similar composite profiles can be achieved for correction of astigmatism. To achieve a correction of astigmatism, the ablative radiation is selectively applied to the eye, in accordance with the astigmatic axis to preferentially flatten the curvature along the axis where the astigmatic bulge is present. Alternatively, the ablative radiation can be applied in accordance with the orthogonal axis to preferentially steepen the curvature along the opposite axis. In either approach at least a partial discontinuity or edge effect will be created at the periphery of the sculpted region.

The laser light source preferably is designed so as to produce pulses of light having substantially constant energy density, such that a known depth of surface material will be eroded for each pulse. By using relatively low power, only a microscopically thin layer of material will be removed in response to each pulse. By continual monitoring and feedback, a very accurate profiling of the cornea can be achieved.

An automatic feedback control system may be provided in which the output from a measuring device for measuring the shape or an optical property of the eye is used to control the delivery of pulses of laser energy. Alternatively, the desired surface profile may be obtained through erosion by a successive approximation technique. In this technique, a measuring device is used to determine the change it is desired to make in the profile of the surface. Pulses of laser energy are delivered to the surface so as to bring about slightly less than the desired alteration. The measuring device is used again to determine the correction now needed to reach the desired profile, and further pulses of laser energy are provided accordingly to produce slightly less than the total calculated correction. This process is repeated until the eroded surface acquires the desired profile to a suitable degree of accuracy.

Suitable measurement devices, commonly called keratometers, are known and commercially available. Examples of such devices include the "Photokeratoscope" manufactured by the Sun Contact Lens Company of Kyoto, Japan, and the "Corneascope" manufactured by International Diagnostic Instruments Limited, Broken Arrow, Okla., USA. (See also, Klyce, "Computer Assisted Corneal Topography," Vol. 25, *Invest. Ophthalmol. Vis, Sci.*, p. 1435 (1984) for a comparison of these instruments and a method of using the "Photokeratoscope").

In order to locate the eye relative to the laser means, conventional suction rings or cups may be used, such as those provided by Steinway Instruments of San Diego, Calif., USA. Alternatively, modified vacuum-fixed stages supporting erodable masks, as described in more detail below, can be used. In either event, the fixation means is typically applied to the white (sclera) region of the eye and connected to a low suction pressure sufficient to clamp the cup or stage to the eye but not so great that the cornea is distorted. The cup or stage may then be fixed to further apparatus (in the present case, this will normally be the optical system of the laser) which will thereby be located accurately with respect to the eye. The use of such devices to immobilize an eye is shown on page 39 of *Ophthalmology Times* of Jul. 1, 1986, and such a procedure is well-known in the art.

Excimer lasers and halogen lasers operating to generate UV radiation are presently preferred for corneal ablation and, in particular, argon-fluoride (ArF) excimer lasers operation at about 193 nm are preferred. In medical uses such as corneal ablation, it is preferred to use an excimer laser which is designed for medical applications, such as the EXCIMED and OMNIMED systems manufactured by Summit Technology, Inc. of Waltham, Mass., USA. (Other lasers such as HF, pulsed $CO_2$, infrared lasers at wavelengths of about 2.6–3.1 μm, Er:YSGG and Er:YAG lasers may also be used.) In most instances, a laser which generates a low divergence beam is desirable. Low divergence can be achieved, for example, by incorporating an astable resonator into the laser cavity.

The pulse repetition rate for the laser may be chosen to meet the needs of each particular application. Normally the rate will be between 1 and 500 pulses per second, preferably between 1 and 100 pulses per second. When it is desired to vary the beam size, the laser pulses may be stopped. Alternatively, the beam size may be varied while the pulses continue. If a measurement device is used to monitor the erosion progress and control the laser system automatically, the beam size may be varied continuously at a controlled rate without interrupting the pulses.

Suitable irradiation intensities vary depending on the wavelength of the laser and the nature of the irradiated object. For any given wavelength of laser energy applied to any given material, there typically will be a threshold value of energy density below which significant erosion does not occur. Above the threshold density, there will be a range of energy densities over which increasing energy densities give increasing depths of erosion, until a saturation value is reached. For increases in energy density above the saturation value, no significant increase in erosion occurs.

The threshold value and the saturation value can vary from wavelength to wavelength of laser energy and from one layer of the cornea to another layer. However, for any particular laser and any particular material, the values can be found readily by experiment.

For example, in the case of eroding Bowman's membrane and stromal portions of the cornea by energy of wavelength 193 nm (the wavelength obtained from an ArF Excimer laser), the threshold value is about 50 mJ per $cm^2$ per pulse, and the saturation value is about 250 mJ per $cm^2$ per pulse. There appears to be little benefit in exceeding the saturation value by more than a small factor, and suitable energy densities at the corneal surface are 50 mJ per $cm^2$ to one J per $cm^2$ per pulse for a wavelength of 193 nm.

The threshold value can vary very rapidly with wavelength, and at 157 nm, which is the wavelength obtained from an $F_2$ laser, the threshold is about 5 mJ per $cm^2$ per pulse. At this wavelength, suitable energy densities at the corneal surface are 5 mJ per $cm^2$ to one J per $cm^2$ per pulse.

Most preferably, the laser system is used to provide an energy density at the surface to be eroded of slightly less than the saturation value. Thus, when eroding the cornea with a wavelength of 193 nm (under which conditions the saturation value is 250 mJ per $cm^2$ per pulse), it is preferable to provide to the cornea pulses of an energy density of 90 to 220 mJ per $cm^2$ per pulse. Typically, a single pulse will erode a depth in the range 0.1 to 1 micrometer of collagen from the cornea.

In one clinical procedure, for example, a laser system capable of measurement and reprofiling to create a region of greater curvature for correction of hyperopia includes one of the above-described laser sources and beam-shaping means, as well as a control unit, a measurement and/or feedback means, and a means for stabilizing the eyeball relative to the beam path. A surgical microscope can be employed to allow the surgeon to aim the laser correctly. After initial setting up and alignment using the microscope and measurement means, reprofiling is effected by appropriate operative signals from the control unit, with remeasurement between either each repro filing step or after a sequence of steps in order to check progress towards the intended final profile of the cornea.

Since reprofiling requires use of a laser beam of changing, cross-sectional area, it is preferred to supply the energy through an optical system which produces a beam having constant energy per unit area regardless of its varying cross-sectional size.

Reprofiling of the cornea can be achieved, for example, by irradiating the cornea through an aperture which may be of adjustable dimensions and shape and/or by using an optical stop which may also be adjustable in size and shape. To achieve a change in the refractive profile of the cornea of an eye, the object is irradiated by a pattern of light which varies with time so that different regions thereof receive different numbers of pulses and are, therefore, eroded to a different extent. Since the normal surface of a cornea is convex, the effect of a concave ablation profile effectively will be to flatten the surface of the cornea slightly. Flattening the surface of the cornea serves to decrease the refractive power of the eye. Conversely, increasing the curvature of the cornea (by effecting a convex erosion pattern), increases the refractive power of the eye.

If a circular iris is placed in the beam directed at the cornea of an eye and the iris is expanded (i.e., opened) while the pulses continue to be delivered, the central region of the cornea, after a given period of time, will have received more pulses (and will, consequently, have been eroded to a greater extent) than the surrounding peripheral regions.

Conversely, if a central stop of adjustable size is placed in the beam path and gradually expanded (e.g., like an umbrella opening slowly into the rain), the peripheral region will, after a period of time, have received more pulses (and, consequently, will have been eroded to a greater extent) than the central region. Thus, by controlling the number of pulses emitted for each setting of the aperture or central stop, the actual profile of the eroded surface of the cornea can be very closely controlled.

Alternatively, a collimated beam of laser energy can be transmitted through an optical system which causes the beam to have a region of divergence, a region of convergence, or both, before it is re-collimated. A beam-shaping element is arranged to move along the beam axis in a region of convergence or divergence. The beam-shaping element may have an aperture or window to provide a variable size shaped beam. Alternatively, it may have a shaped stop portion where the beam is to be provided with a region of reduced or zero illumination of variable size. Combinations of apertures and stop portions may be provided if a more complex beam shape is required.

For convenience, the following description is in terms of a beam-shaping stop, but other types of stops will function in an analogous manner.

As such, a stop is moved along the axis of the beam, the beam diameter at the position of the stop will vary. Thus, when the stop is at one end of its range of travel (where the beam diameter is smallest), all (or a relatively large portion) of the beam will be passed, whereas when the stop is at the other end of its range of travel (maximum beam diameter), only a relatively small portion of the beam will pass the stop.

Only that portion of beam which passes the stop is re-collimated and, thus, moving the stop axially along the beam will vary the size of the collimated output beam. The shape of the collimated output beam will be governed by the shape of the stop. Since the portion of the laser beam passing the stop is unaffected by it, the stop has no effect on the energy density of the beam but merely on its size.

Alternatively, the input beam may be uncollimated, in which case the optical elements of the system will have slightly different powers so as to ensure that the output beam is substantially collimated.

Since the shape of the beam delivered to the surface will correspond to the shape of the stop, a wide range of beam shapes is available.

Another approach to increasing the curvature of a cornea to correct hyperopia can employ a concave lens, or other beam-shaping device, to create an annular region of illumination with a central region having zero or minimal illumination. By using a complementary convex conical lens in combination with a concave conical lens, the diameter of the illuminated annulus can be adjusted by altering the axial distance between the convex conical lens and the concave conical lens.

Alternatively, mirrors may be used. A mirror having an elliptical aperture may be located at 45 degrees to the illumination axis of the laser and positioned relative to the corneal surface which is to be irradiated, so that the image of the hole in the center of the mirror is coincident with the center of the region of the surface which is to be exposed. The size of the illuminated annulus can be altered by changing the mirror. A mirror is especially useful for providing a variable width non-illuminated strip. Two mirror portions may be provided separated by a gap which results in the non-illuminated strip. By moving the mirror portions towards and away from each other, the width of the strip can be varied.

Where differential erosion is to be effected parallel to a line rather than around a point, cylindrical lenses or plain mirrors or slits may be used to produce rectangular or otherwise asymmetric erosion profiles. Such techniques can be employed on a cornea to correct astigmatism and the like.

The various beam-shaping elements discussed above are described in more detail in the above-referenced U.S. Pat. No. 4,941,093, again herein incorporated by reference.

In another approach a rotating mask can be used to modify the spatial intensity distribution of the ablative beam of radiation. In one aspect, a mask having at least one transmissive aperture is rotated about a rotation point that is co-aligned to the beam, preferably at its center. The aperture originates substantially at the rotation point and forms a geometric spiral shape which expands outwardly. The aperture further has a transmissive width which changes progressively along the length of the spiral shape. As the mask is rotated about the rotation point, a beam of radiation incident on the mask is transmitted therethrough with the intensity that varies in accordance with the design or properties of the mask and as a function of radial position with respect to the rotation point. For a more detailed explanation of rotating mask systems, see International Patent Application No. PCT/US94/06298 by Peter J. Klopotek, herein incorporated by reference.

Alternatively, the beam-shaping means of the present invention can comprise a masking means disposed between the laser means and the corneal surface for providing a predefined profile of resistance to erosion by laser radiation, such that, upon irradiation of the masking means, a portion of the laser radiation is selectively absorbed and another portion is transmitted to the surface in accordance with the mask profile to selectively erode the surface.

The masking means can further comprise a rigid structure which is affixed to the surface, in particular to the sclera of an eye, and a masking lens connected to the support structure and disposed above the cornea. The mask can be directly integrated with the support structure or, preferably, a transparent stage can be formed as part of the support structure to support and position the masking lens.

The masking means of the present invention provides a predefined profile of resistance (e.g., by erosion or photoabsorption) to laser radiation. Such profiles can be provided by varying the thickness or composition of the mask material. To provide the hyperopia correction necessary to accommodate close viewing of objects in at least a portion of the optical zone, the mask should provide at least one region in which the corneal curvature is steeper.

When the thickness of the mask is varied, an steepened region can be provided, for example, by a convex or plano-convex shaped mask or by a mask which is aspherical or torroidal on at least one surface. Alternatively, the composition of the mask can be varied, for example, by incorporating more photoabsorptive elements into the portion of the mask which is aligned with the center of the desired add region. To correct composite refractive errors, such as correction of both astigmatism and myopia, or astigmatism and hyperopia, composite masks of more complex but readily ascertainable shapes can be employed, or two or more separate masks can be used simultaneously or sequentially.

When erodable masks are employed, the mask material preferably has similar ablation characteristics to the cornea. Various polymeric materials can be employed as erodable masks, including, for example, poly(methyl methacrylate), poly(methyl styrene) and mixtures thereof. The ablation characters will be govern by the absorption coefficients. For corneal repro filing, the absorption coefficient of the masking material can range from about $10^4$ to about $10^{5\ cm^{-1}}$. Preferably, the masking material has an absorption characteristic of micron or submicron etch depths per pulse similar to those of the cornea when it is exposed pulsed UV excimer laser radiation.

Figure 1:
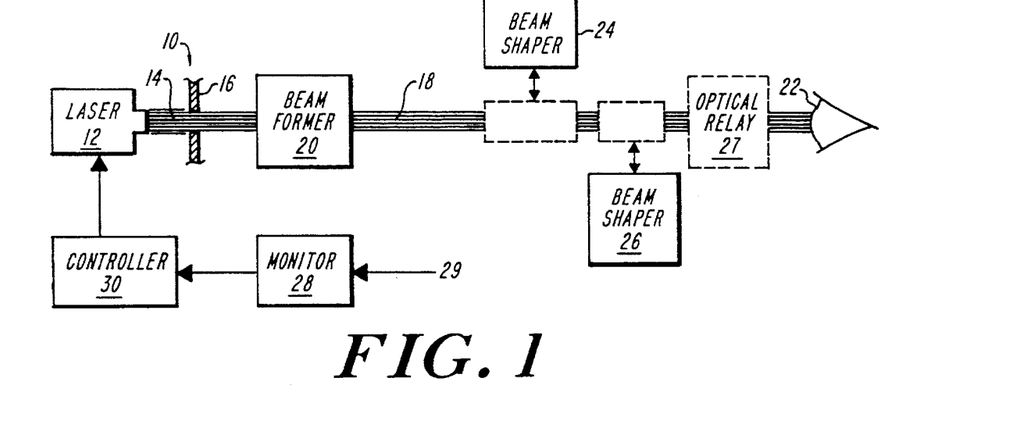
FIG. 1 is a schematic illustration of an apparatus for reprofiling the surface of a cornea in accordance with the present invention.

In FIG. 1, a system for performing photorefractive keratectomy is shown, including a laser 12 which provides a radiation output 14. The system 10 can further include an initial beam-clipping aperture 16 to generate a more uniform output beam. The system 10 can further include a beam-forming element 20 which preferably operates to produce a collimated beam of uniform cross-section and low divergence. (Beam-forming systems including anamorphic lens assemblies are disclosed in U.S. Pat. No. 4,941,093, herein incorporated by reference.) The system 10 further includes a first beam-shaping assembly 24, suitable for reprofiling the cornea to change the overall curvature, and a second beam-shaping assembly 26, for generating an annular beam of ablative radiation. As shown, elements 24 and 26 can be disposed in the beam path or removed by the clinician to permit sequential operations. (Although the elements are shown with a relative axial displacement from each other for illustration, it should be clear that the beam-shaping elements 24 and 26 can be disposed interchangeably or, alternatively, in the same location along the beam path at different times during the procedure.) Optionally, the system 10 further includes an optical relay assembly 27 which serves to either project or image the output of the beam-shaping elements 24 and 26 onto the surface of a cornea 22.

The laser 12 can be powered and controlled by controller/power supply 30, which can be adjustable to cause the laser to produce pulses of light at a specific frequency and/or intensity. To further control the laser 12, a monitor 28 can be provided which receives measurement signals 29 from the beam-shaping means and/or the cornea while it is exposed to a radiation by the laser 12. The monitor 28 generates a control signal which is communicated to the controller 30 for controlling the laser 12 and/or optionally for controlling the beam-shaping means.

In use, the system 10 can operate to reprofile the surface of the cornea 22 to correct refractive errors in vision, such as hyperopia or astigmatism. In such procedures, the first beam-shaping system 24 would normally operate to provide a reprofiled corneal surface having a steeper curvature along at least one axis. This operation would be complimented by the second beam-shaping system 26 which would create a blend zone between the outer edge of the reprofiled region of the cornea and the peripheral unablated corneal surface. In doing so, the system of the present invention ensures that a smooth corneal surface is preserved to promote epithelial cell regrowth and to minimize the degree to which healing processes induce regressive refractive changes. (In some instances, the annular beam-shaping system 26 can be used alone to treat mild forms of hyperopia and/or astigmatisms by appropriate design of the beam-shaping element.)

Figure 2A:
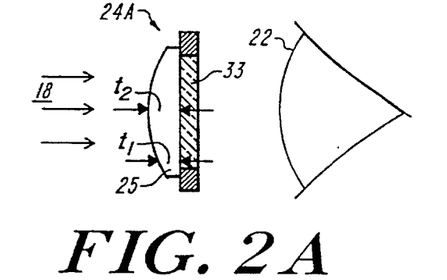
FIG. 2A is a more detailed illustration of a masking means for selectively transmitting ablative radiation to the cornea.
Figure 2B:
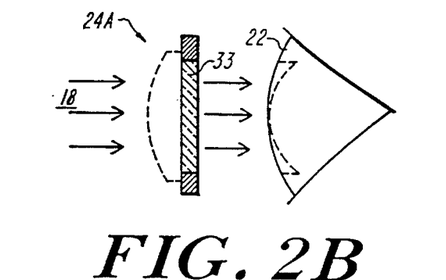
FIG. 2B illustrates diagrammatically the method of beam shaping employed by the mask of FIG. 2A and its effects on the cornea to steepen the corneal surface curvature.

In FIGS. 2A and 2B, one embodiment of a beam-shaping apparatus 24A is shown for hyperopic correction. The apparatus 24A includes a mask element 25 which is erodible or otherwise has a profile of resistance to the ablative radiation 18 which is progressively destroyed. When aligned with the laser, as shown in FIG. 1, the mask 25 selectively transmits a pattern of ablative radiation to the cornea. As shown, mask 25 can be mounted upon a transparent stage 33 which allows laser radiation to pass through to the cornea. (Although the transparent stage 33 is substantially vertical, it should be clear that the mask can likewise be disposed in a horizontal position to transmit light downward onto a patient's cornea.) In use, the mask 25 is gradually ablated, or otherwise rendered transparent to radiation 18, such that an increasing area of radiation passes through the transparent stage 33 and irradiates the cornea.

As shown in FIG. 2B, once the mask is wholly eroded or rendered transparent, the surface of the cornea is eroded as indicated to complete the reprofiling. As shown in FIGS. 2A–2B, the maximum thickness $t_1$ of the mask 25 exceeds the minimum thickness $t_2$ by an amount equal to the maximum depth of corneal erosion, if the procedure was stopped as soon as the mask is eliminated. By controlling the shape, thickness and/or composition of the mask 25, photoablation of the cornea can be precisely confined to a particular sculpting action.

Figure 3:
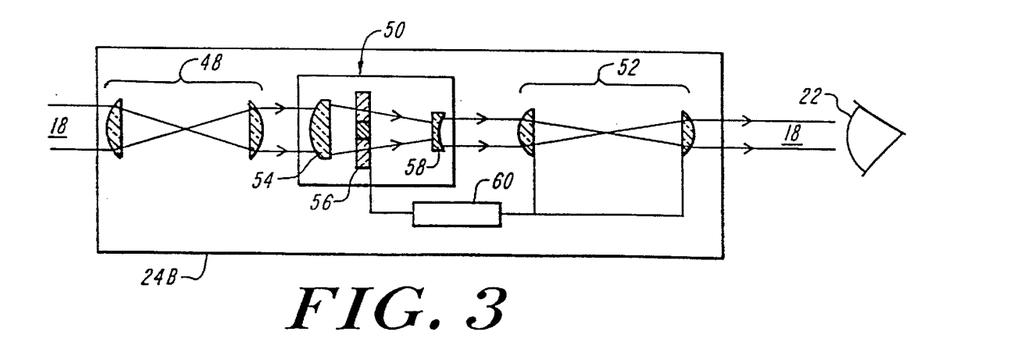
FIG. 3 illustrates a beam-shaping assembly for varying the size of the exposure area of a beam of ablative radiation upon the cornea.

In FIG. 3, another beam-shaping means 24B is shown for use in the system of FIG. 1, to again reprofile the corneal surface. In this embodiment, the laser light 18 passes through the optical elements of the beam-shaping means 24B to create an output beam of desired shape and size. Output beam 18 is delivered to the surface of the cornea 22.

The beam-shaping element 24B of FIG. 3 can include a first relay telescope 48 which delivers the beam to a dimension control means 50. The dimensional control means 50 can include, for example, a plano-convex lens 54 and a plano-concave lens 58, which cooperate to define a converging (or, alternatively, a diverging) beam portion between them.

A stop 56 (e.g., a transmissive element having a central opaque region) is movable along the beam axis over the converging beam portion. In order to vary the size of a ring-shaped exposure area on the cornea, the stop 56, having an annular aperture, is moved axially along the beam between the lenses 54 and 58. When the stop 56 is adjacent to the plano-concave lens 58, the plane of the stop intersects the converging beam at its smallest diameter. Thus, a relatively small annular portion of the beam passes through the stop 56 as the remainder strikes the stop and is absorbed or deflected. However, if the stop is moved so as to be adjacent to the plano-convex lens 54, the plane of the stop intersects the converging beam at its greatest diameter. In this position a relatively large portion of the laser beam passes through the aperture in the stop 56. In either position, the central portion of the beam is not passed through the aperture, and it should be evident that so long as the input beam is collimated and substantially uniform in its cross-sectional intensity, the stop will not affect the energy density of the transmitted beam regardless of the thickness of the annulus projected or imaged onto the eye.

From the beam-shaping means 50, a second relay telescope 52 delivers the output beam 18 to the cornea 12. Since the stop 56 is moved axially along the beam to vary the size of the illuminated area on the surface of the cornea, the second relay telescope will not always provide a precisely focused image of the aperture in the stop 56, if the telescope has a fixed focal length. Accordingly, a gearing arrangement 60 can be provided to synchronize the movement of the stop 56 with the corresponding movement of the elements of the second relay telescope to maintain an in-focus image on the cornea 22.

Figure 4:
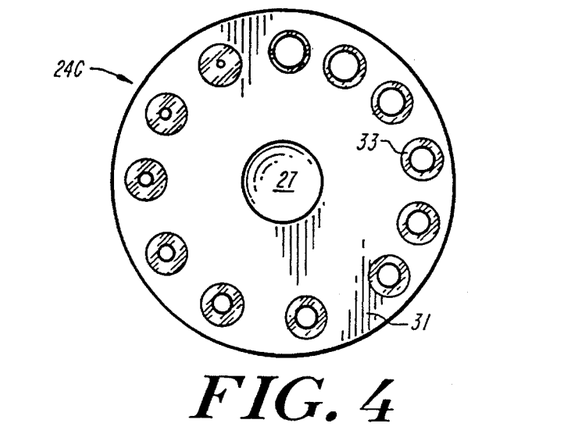
FIG. 4 is an illustration of an aperture wheel having a series of annular apertures which can also be used to vary the exposure area on the cornea over time.

In FIG. 4, another alternative beam-shaping means 24C is shown comprising an aperture wheel which is disposable such that particular apertures can be aligned with the output beam 18 of the system 10 shown in FIG. 1. As shown, the aperture wheel 24C includes a plate 31 and a plurality of stops 33, each of which defines an annular transmissive region of different size. (Although the annular shapes shown in FIG. 4 are circular; it should be clear that various other shapes can also be employed, including, for example, elliptical rings of varying width to treat astigmatic corrections by asymmetric ablation.)

Figure 5A:
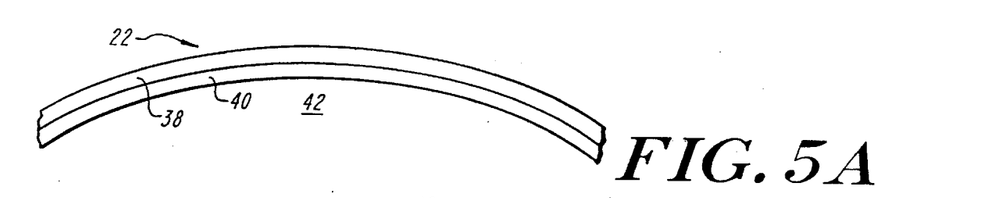
FIGS. 5A–5D show how different profiles can be obtained by altering the size of the annular exposure area upon the cornea over time and further illustrate the surface discontinuities which can occur at the boundary between the ablated and unablated regions.
Figure 5B:
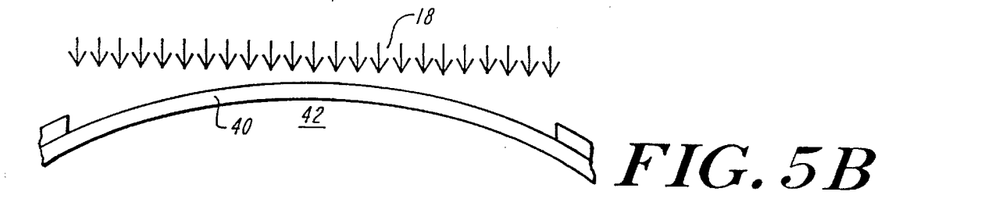

FIGS. 5A–5D are schematic illustrations of how the beam-shaping means of FIGS. 3 and 4 can operate to create hyperopic correction in a selected portion of the cornea 22 by increasing the curvature of the cornea in this region. In FIG. 5A, the intact surfaces of the cornea are shown comprising the epithelium 38, Bowman's membrane 40 and the upper portion of the stroma 42. In FIG. 5B, a large aperture is employed to ablate all (or a substantial portion) of the epithelial layer 38 of the cornea 22 in the selected region of the optical zone so as to expose the surface of Bowman's membrane 40.

Figure 5C:
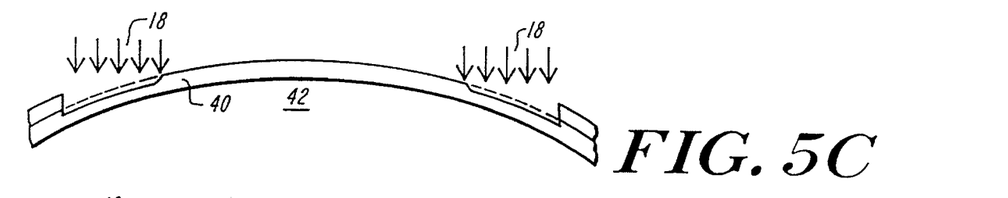
Figure 5D:
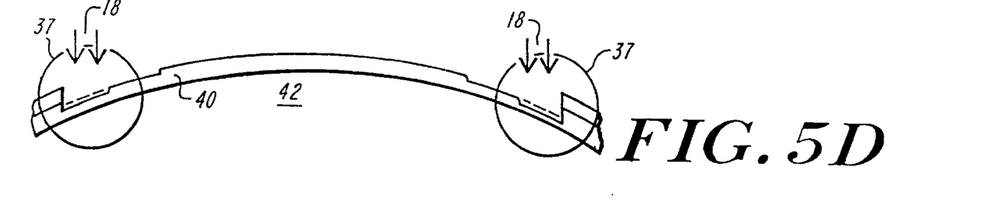

A first annular ablation region of wide cross-sectional areas is then created in Bowman's membrane, as shown in FIG. 5C. A narrower ring of further ablation is then created as shown in FIG. 5D, to create a steepened curvature. Thus, a stop having a central beam-stopping region is employed to create a ring-like ablation zone which is shifted to the periphery of the optical zone so as to create a "hail-like" profile of ablation, thereby steepening the curvature of the cornea upon regrowth of the epithelial layer over the resculpted corneal surface.

In FIGS. 5A–5D, the ablation profile is confined to the Bowman's layer membrane 40 of the cornea. However, it should be clear that some hyperopic (or astigmatic) corrections will require deeper ablation and penetrate into the stroma proper 42. It should also be clear that the actual procedure is carried out with a substantially greater number of steps than shown in FIGS. 5A–5D to achieve a smooth curve and minimize the step-effects. Additionally, the order of the steps can be reversed, e.g., by starting with a very narrow peripheral ablation ring and then gradually increasing inwardly the thickness of the annular beam.

Regardless of the technique, however, a surface discontinuity 37, as shown in FIG. 5D will result. For hyperopic corrections, this surface discontinuity will manifest itself as a rim or groove in the cornea at the boundary between the ablated and unablated regions. For astigmatic corrections, the discontinuity will be an arcuate groove. Upon completion of the laser surgery, the epithelium will attempt to regrow with a uniform thickness over the reprofiled surface. However, when it encounters a surface discontinuity, such as the edge effect 37 shown in FIG. 5D, difficulties arise. Either the epithelium is unable to regrow properly or it will tend to fill in the groove with additional layers of cells and thereby reduce the effectiveness of the corneal reprofiling operation.

Figure 6:
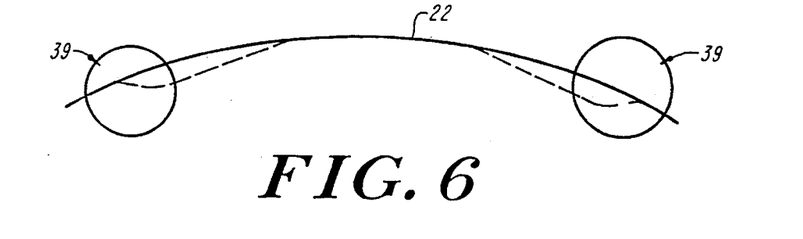
FIG. 6 illustrates the formation of a blend zone according to the present invention to alleviate surface discontinuities.

Therefore, it is desirable to create a blend zone as shown in FIG. 6. The blend zone 39 ensures that the new curvature is maintained within the optical zone while creating a new curve at the periphery that allows a smooth transition to occur between the ablated and unablated regions of the cornea 22.

Figure 7:
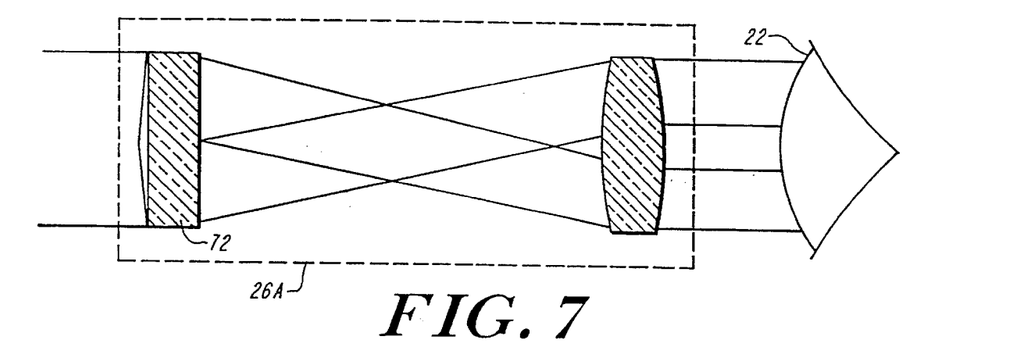
FIG. 7 illustrates an annular-beam-shaping assembly for use in the present invention.

In FIG. 7, a beam-shaping system for 26A for generating an annulus of radiation is shown consisting of a lens element 72 and, optionally, a second collimating lens 74. Lens 72 is designed to convert the input laser radiation 18 into an annular beam. This annular beam is then projected by lens 74 onto the cornea. (It should be clear that various other lens elements can be employed either in place of lens 74 or in addition to lens 74 in order to relay the annular beam to the eye. Such lens systems can either be projection-mode optical systems or imaging systems.)

Figure 8:
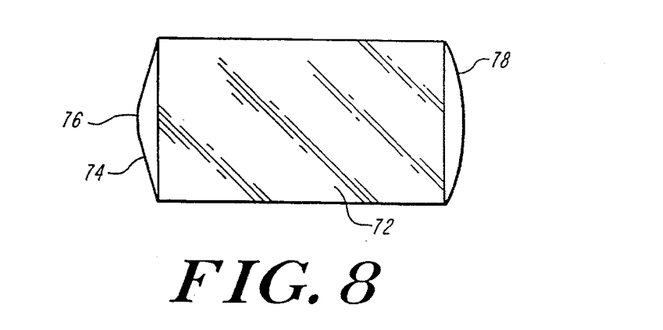
FIG. 8 is an expanded view of the annulus-forming lens of FIG. 7 with a roughly 5:1 horizontal scale expansion.

In FIG. 8, the lens element 72 is shown in an expanded shape (with the horizontal dimensions being enlarged by a factor of about 5:1 in order to illustrate the shape of the from and rear faces of the lens). As shown, the from face of lens 72 includes a conical section 74 and a flat central region 76. The size of this center region 76 is variable, depending upon the shape of the annulus desired. In some instances, it may be preferable to treat this flat region 76 with a reflective coating. The rear face of lens 72 has a slight curved surface 78. Together, the conical front face and the curved rear face, cooperate not only to generate an annulus of radiation but to insure that the radiation intensity profile will vary.

Figure 9:
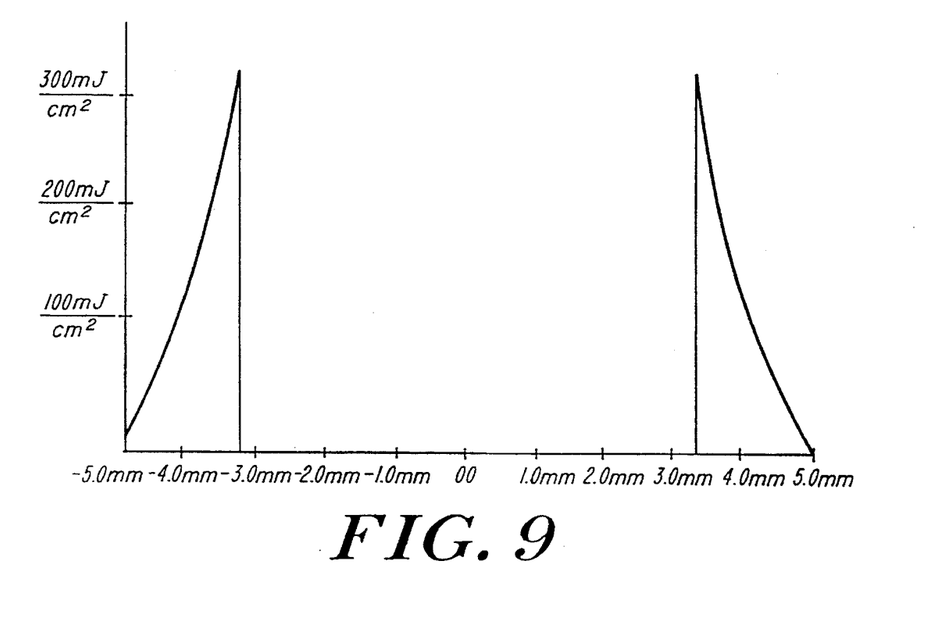
FIG. 9 is a computer-simulated graph of energy density versus axial location for an annular beam of ablative radiation in accordance with the present invention.

In FIG. 9, the variation in intensity is illustrated graphically. FIG. 9 is a computer generated simulation of the intensity profile of an annulus of radiation generated with a lens such as shown in FIGS. 7 and 8. As shown, the annular beam has essentially zero intensity in the central region (e.g., within about 3 mm in radius from the optical axis). The intensity quickly peaks at the inner segment of the annulus and then progressively decreases to nearly zero at the outer edge (5.0 mm from the optical axis).

Figure 10:
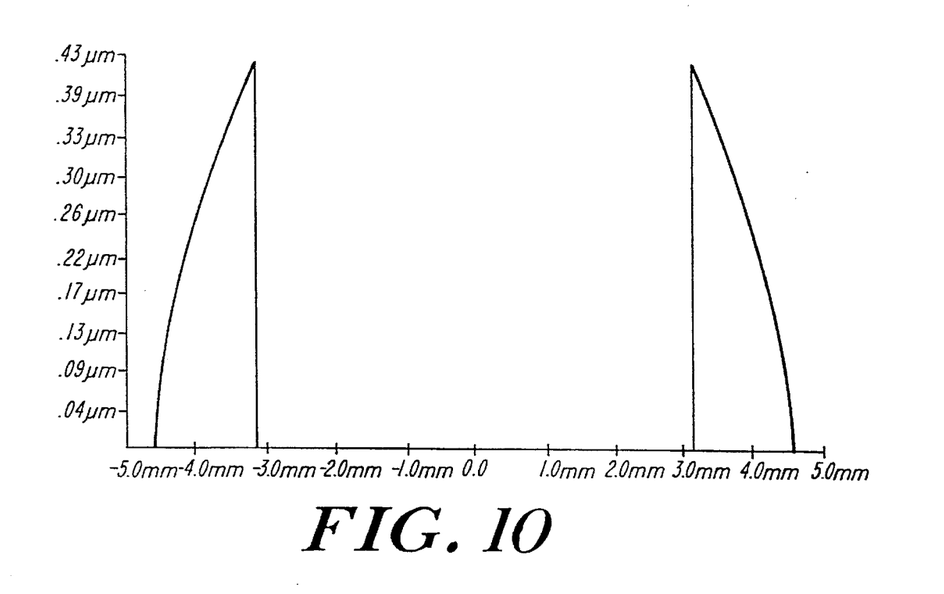
FIG. 10 is a computer-simulated graph of ablation depth versus radial distance from the optical axis for an annular beam as illustrated in FIG. 9.

In FIG. 10, the ablative effects of the beam shown in FIG. 9, are also generated by computer simulation. Using the beam emitted by this lens element, there would be zero ablation of the central optical zone (where reprofiling operations would have been performed). As one moves further out from the optical axis on the cornea, the annular ablation beam would have its most significant effects at about 3.4 mm (corresponding to the area where a cliff-like edge would be most pronounced following hyperopic corrections) and then the ablative effects of the annulus drop off until about 4.5 mm from the optical axis, where the effects would be insignificant. Thus, this ablation profile would effectively create the desired blend zone as illustrated in FIG. 6.

Figure 11:
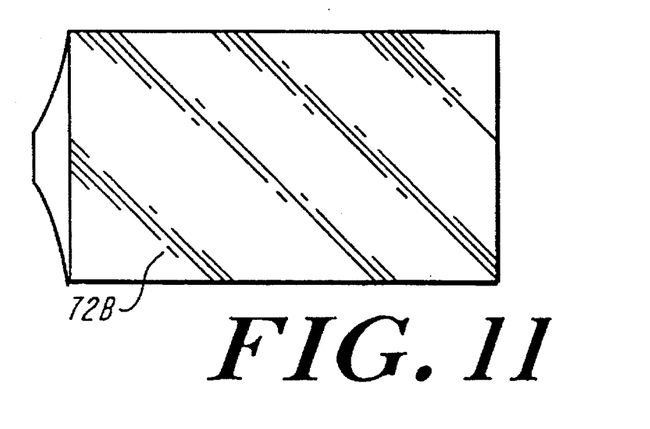
FIG. 11 is another expanded view of a lens element useful in producing an annular beam having a variable intensity profile.
Figure 12:
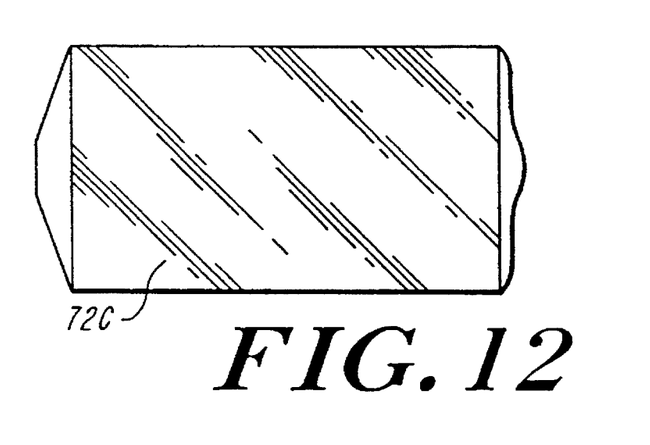
FIG. 12 is another expanded illustration of a lens element for producing a variable intensity annulus of ablative radiation.
Figure 13:
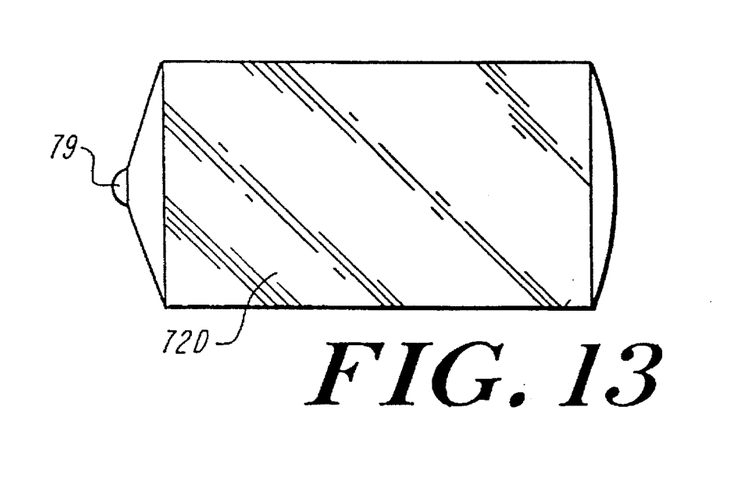
FIG. 13 is yet another expanded illustration of an alternative embodiment of the annulus-producing lens.

In FIG. 11, another alternative embodiment of 72B of the above-described annulus-generating lens is generated. In this embodiment, the front face of the lens has a slightly curved surface. In FIG. 12, a further embodiment 72C is illustrated in which the rear face has a complex curved surface. The designs of FIGS. 11 and 12 are useful to generate more complicated ablation profiles. For example, such profiles can be designed by appropriate choice of either the front or rear surface, or both, to compliment any ablation profile that may have already been formed in the eye (or will be subsequently be formed in the eye) as part of the curvature correcting process. In FIG. 13, a further alternative embodiment 72D is shown in which the flat or truncated cone region on the front face of the lens has been replaced with a hemispherical reflector 79. This hemispherical reflector can be useful to scatter the radiation impinging on the center of the lens in such a way that it can be rapidly absorbed by traps (not shown) in the surrounding support structure.

We claim:

1. In a system for photorefractive keratectomy having a source of ablative laser radiation and a means for selectively reprofiling a cornea of an eye by removing a volume of corneal tissue from a region in an optical zone of the cornea with ablative radiation to form a reprofiled region which modifies, at least in part, a central curvature of the cornea; the improvement comprising means for applying to a peripheral region of the cornea an annular beam of ablative radiation having an intensity which varies radially within the annulus of the beam to create a blend zone, thereby permitting a smooth transition between the reprofiled region and an unablated region of the cornea.

2. The system of claim 1 wherein the means for applying to a peripheral region of the cornea an annular beam of ablative radiation further comprises a lens element having a front face and a rear face, the front face being conical such that a light beam incident on the front face along an optical axis will be refracted into an annular beam.

3. A method of photorefractive keratectomy comprising (a) selectively reprofiling a cornea of an eye by removing a volume of corneal tissue from a region in an optical zone of the cornea with ablative radiation to form a reprofiled region which modifies, at least in part, a central curvature of the cornea; and (b) applying to a peripheral region of the cornea an annular beam of ablative radiation having an intensity which varies radially within the annulus of the beam to create a blend zone which provides a smooth transition between the reprofiled region and an unablated region of the cornea.

4. The method of claim 3 wherein the step of reprofiling the cornea further comprises varying the size of an annular exposure area on the cornea over time.

5. The method of claim 3 wherein the step of reprofiling the cornea further comprises selectively transmitting ablative radiation through a mask onto the cornea.

6. The method of claim 5 further comprising the step of rotating the mask.

7. The method of claim 5 wherein the mask has a profile of resistance to ablative radiation which is progressively destroyed.

8. The method of claim 3 wherein the step of creating a blend zone further comprises applying an annular beam to the peripheral region of the cornea which has, at least in part, a radially decreasing intensity profile.

9. The method of claim 3 wherein the step of creating a blend zone further comprises applying an annular beam to the peripheral region of the cornea which has, at least in part, a radially increasing intensity profile.

10. The method of claim 3 wherein the step of creating a blend zone further comprises applying an annular beam to the peripheral region of the cornea which has an intensity profile which first increases and then decreases as a function of radial distance from axis.

11. The method of claim 3 wherein the step of creating a blend zone further comprises applying an annular beam to the peripheral region of the cornea which has an intensity profile that provides a compliment to the reprofiling step and achieves a blend zone by cumulative action.

12. The method of claim 3 wherein the step of reprofiling of the optical zone is performed before applying the annular beam to define the blend zone.

13. The method of claim 3 wherein the step of applying the annular beam of ablative radiation is performed before reprofiling of the optical zone.

* * * * *